United States Patent [19]

Redmore et al.

[11] 4,076,638

[45] Feb. 28, 1978

[54] OIL-SOLUBLE ALUMINUM COMPOSITIONS

[75] Inventors: Derek Redmore, Ballwin; Frederick T. Welge, Webster Groves, both of Mo.

[73] Assignee: Petrolite Corporation, St. Louis, Mo.

[21] Appl. No.: 616,174

[22] Filed: Sep. 22, 1975

[51] Int. Cl.$^2$ .............................................. C10M 1/40
[52] U.S. Cl. .................................. 252/33.2; 252/33; 252/33.4; 252/35; 252/354; 260/429 K; 260/448 R
[58] Field of Search .............. 260/448 R, 429 K, 414; 252/33, 33.4, 354, 33.2

[56] References Cited

U.S. PATENT DOCUMENTS

| | | | |
|---|---|---|---|
| 1,438,101 | 12/1922 | Divine | 260/438.5 R |
| 2,367,470 | 1/1945 | Neely et al. | 260/429 K X |
| 2,507,030 | 5/1950 | Lynch | 260/481 |
| 2,760,970 | 8/1956 | Le Suer | 260/429 |
| 3,038,899 | 6/1962 | Sifford | 260/429 R |
| 3,867,296 | 2/1975 | Hunt | 252/33.4 |

OTHER PUBLICATIONS

Chemical Abstracts, 68, 14029g (1968).

*Primary Examiner*—Helen M. S. Sneed
*Attorney, Agent, or Firm*—Sidney B. Ring; Hyman F. Glass

[57] ABSTRACT

This invention relates to the preparation of oil-soluble aluminum compositions of high aluminum content, such as from about 15 to 25% aluminum; to the resulting products; and to the use of such products, for example, as fuel additives such as additives employed in turbine fuel as corrosion inhibitors and other uses.

17 Claims, No Drawings

OIL-SOLUBLE ALUMINUM COMPOSITIONS

Oil-soluble aluminum compositions have been prepared by a wide variety of methods. One method is described in U.S. Pat. No. 3,867,296 which is summarized in claim 1 thereof as follows:

A process for preparing clear, bright aluminum-containing dispersions containing at least 6 weight percent aluminum, said process comprising:

a. admixing an oil soluble dispersing agent, selected from the group consisting of oil soluble sulfonic acids in which the hydrocarbon portion has a molecular weight between about 350 and 1000 and hydrocarbyl carboxylic acids containing at least 8 carbon atoms, an oleaginous carrier selected from the group consisting of mineral lubricating oils, synthetic lubricating oils, vegetable oils and animal oils and a volatile hydrocarbon solvent having a boiling point at atmospheric pressure below about 300° F. with alumina prepared by the water hydrolysis of aluminum alkoxides and having the following properties:

| (1) Crystal structure | alpha alumina monohydrate |
|---|---|
| (2) Crystal structure after calcining to 900° F | gamma alumina |
| (3) Ultimate crystal size (x-ray diffraction) | |
| 020 reflection | 30–70A |
| 021 reflection | 60–110A |
| (4) Pore volume | 0.35–0.65 cc/g |
| (5) Loose bulk density | 37–70 lb/ft' |
| (6) Particle size (sieve) | |
| > 45 micron | 20% |
| < 45 micron | 80% |
| (7) $Al_2O_3$ content | 65–85 wt. % |
| (8) Loss on Ignition | 15–35 wt. % |
| (9) Surface Area | 150–350 $m^2$/g | to form a mixture of uniform consistency;

b. heating said mixture to remove substantially all of said volatile hydrocarbon solvent and c. recovering said clear bright aluminum-containing dispersion.

We have now discovered a method for the preparation of oil-soluble aluminum compositions containing high aluminum concentration such as for example from about 15 to 25% aluminum.

Our process comprises reacting alumina with a solution of both a carboxylic acid and a sulfonic acid. In practice, the reaction mixture is heated and the solvent removed by distillation.

We have further discovered that our process has the following major differences from that disclosed in U.S. Pat. No. 3,867,296:

1. That the use of a mixture of both carboxylic and sulfonic acids in the present invention is superior to either component employed separately;

2. That sulfonic acids of lower molecular weights than those disclosed in U.S.Pat. No. 3,867,296 are not only employed but are the preferred reagents;

3. That no oleaginous carrier is employed since we find it deleterious;

4. That substantially no water is employed;

5. That products of higher aluminum content are obtained than by U.S. Pat. No. 3,867,296.

6. That carboxylic acids of significantly higher melting point than disclosed can be employed. For example, U.S. Pat. No. 3,867,296 states on Col. 4, l. 1-4: "For producing the dispersions of this invention in liquid form, I prefer fatty acids which are liquid at ambient temperatures down to about 15° C." In the present application stearic acid having a 69° C. melting point is employed.

Suitable carboxylic acids which can be used in preparing the aluminum dispersions include naphthenic acids, such as the substituted cyclopentane monocarboxylic acids, the substituted cyclohexane monocarboxylic acids and the substituted aliphatic polycyclic monocarboxylic acids containing at least 15 carbon atoms. Specific examples include cetyl cyclohexane carboxylic acids, dioctyl cyclopentane carboxylic acids, dilauryl decahydronaphthalene and stearyl-octahydroindene carboxylic acids and the like and oil-soluble salts thereof. Suitable oilsoluble fatty acids are those containing at least about 8 carbon atoms. Specific examples include 2-ethyl hexanoic acid, pelargonic acid, oleic acid, palmitoleic acid, linoleic acid and reconoleic acid. Naturally occurring mixtures of predominantly unsaturated fatty acids, such as tall oil fatty acids, are particularly suitable. Examples of commercially available tall oil fatty acids include the "Crofatols," available from Crosby Chemical Company and the "Acintols," available from Arizona Chemical Company.

Volatile solvent as used herein refers to hydrocarbon and oxy-hydrocarbon solvents having a boiling point at normal atmospheric pressure of less than about 300° F. Some specific examples of such solvents are: petroleum naptha, hexane, heptane, octane, benzene, toluene, glycol ethers, monohydric alcohols containing from about 1 to about 6 carbon atoms and the like. Very desirable solvents are hexane, heptane, benzene, toluene, xylene, butanol and the monomethyl ether of ethylene glycol.

The dispersible alumina useful in the process of the present invention is prepared by the water hydrolysis of aluminum alkoxides prepared by the Ziegler process to produce an organic portion and an aluminum slurry portion. The alumina slurry portion is further purified and dried. Careful control of this process results in alumina which can be used to prepare the oil soluble dispersions of the present invention. Such an alumina is marketed by Continental Oil Company of 30 Rockefeller Plaza, New York, N.Y. under the trademark "DISPAL." The physical properties of such alumina are typically as follows:

| (1) crystal structure | alpha alumina monohydrate |
|---|---|
| (2) crystal structure after calcinating to 900° F | gamma alumina |
| (3) Ultimate crystal size (x-ray diffraction) | |
| 020 reflection | 30–70A |
| 021 reflection | 60–110A |
| (4) Pore volume | 0.35–0.65 cc/g |
| (5) loose bulk density | 35–70 lb/ft$^3$ |
| (6) particle size (sieve) | |
| > 45 micron | 20% |
| < 45 micron | 80% |
| (7) $Al_2O_3$ content | 65–85 wt. % |
| (8) Loss on ignition | 15–35 wt. % |
| (9) Surface area | 150–350 in$^2$/g. |

It has been found that uniquely desirable aluminum dispersions are produced by the process of the present invention when such alumina is used. Tests with other alumina products have failed to yield comparable products.

In contrast to U.S. Pat. No. 3,867,296 where "oil-soluble sulfonic acids" are defined as "those materials wherein the hydrocarbon portion of the molecule has a molecular weight in the range of about 300 to about 1000, preferably, this molecular weight is in the range of about 370 to about 700" the preferred sulfonates of the present invention have a hydrocarbon portion whose molecular weight is below 300. For example, the preferred sulfonate, dodecyl benzene sulfonate, has a hydrocarbon portion having a molecular weight of 245 which is below the minimum values stated in U.S. Pat. No. 3,867,296.

Examples of hydrocarbon groups of the sulfonic acids include alkyl, aryl, alkaryl, aralkyl, cycloalkyl, etc. groups, as illustrated by the following specific examples:
octyl
decyl
dodecyl
tetradecyl
hexadecyl
octadecyl
octyl phenyl
nonylphenyl
decylphenyl
dodecylphenyl
tetradecylphenyl
dipropylnaphthyl
dibutylnaphthyl
dioctylnaphthyl, etc.

Although we prefer a hydrocarbon moiety which has a molecular weight of less than about 300, the higher sulfonic acid disclosed in U.S. Pat. No. 3,867,296 may be employed but are not preferred.

The molar ratio of sulfonic acids are carboxylic acids can vary widely, such as from about 10:1 to 1:10, for example from about 5:1 to 1:5, but preferably from about 4:1 to 1:4.

Although U.S. Pat. No. 3,867,296 employs water and oleaginous carriers, these are preferably omitted from the present process. When employed, the presence of water and oleaginous carriers in the reaction mixtures yield inferior products in respect to higher viscosities for a given aluminum content. In other words, higher aluminum contents, up to 25%, can be obtained while keeping the viscosity relatively low. The advantage of lower viscosities is extremely important since it allows the high aluminum content reaction products of this invention to be handled with greater facility since they can be poured.

The following examples are presented for purposes of illustration and not of limitation.

EXAMPLE 1

To a solution of dodecylbenzene sulfonic acid (21.4g; 0.066 mole) and Sunaptic acid B (6.2G; 0.0165 mole) in xylene (200 ml) was added Dispal alumina (82.5g) while providing good agitation. The mixture was heated under reflux for 1½ hours and the solvent removed. Centrifugation removed undispersed solid (3g). The final product was a bright solution of moderate viscosity. 146g. containing 21.4% aluminum. This product was readily diluted with hydrocarbon solvents to yield clear sediment-free solutions.

EXAMPLE 2

Use of Benezene as Solvent

Dispal alumina (82.5g) was added with stirring to a solution of Sunaptic acid B (6.2g) and dodecylbenzene sulfonic acid (21.4g) in benzene (200 ml). The mixture was heated at reflux for 2 hours, insolubles removed by centrifugation (5g) and solvent removed to yield a free flowing bright liquid. Aluminum content was 21.8%.

EXAMPLE 3

This procedure was identical to that used in Example 1, but in which Crofatol P (fatty acid mixture from tall oil) was substituted for Sunaptic acid. The aluminum content of the final product was 21.5% and sediment removed by centrifugation 2.1g.

EXAMPLE 4

To a solution of Sunaptic acid B (6.2g) and dodecylbenzene sulfonic acid (21.4g) in xylene (200 ml) was added Dispal alumina (50g) and the mixture stirred at reflux for 1½ hrs. Centrifugation removed. 4g insolubles and distillation of the solvent left 106.4g of product with aluminum content 17.8%.

The following table summarized the results of a study in which the ratio of sulfonic acid (dodecylbenzene sulfonic) to naphthenic acid (Sunaptic B) was varied. The procedure used was that of Example 4 in which mole ratio of acids to Al was 1:9.1.

| Ex. | Mole% SO$_3$H | Mole% CO$_2$H | Aluminum Content | Yield* |
|---|---|---|---|---|
| 5 | 100 | 0 | 16.2% | 93% |
| 6 | 80 | 20 | 17.8% | 92% |
| 7 | 75 | 25 | 17.3% | 90% |
| 8 | 50 | 50 | 17.4% | 96% |
| 9 | 33 | 66 | 13.7% | 95% |
| 10 | 25 | 75 | 12.8% | 90% |
| 11 | 0 | 100 | 15.4% | 50% |

*Percentage of Al$_2$O$_3$ charged in final soluble product.

The results in this table clearly show that a combination of sulfonic acid and carboxylic acid is superior to either used alone, when used in mole ratios of sulfonic to carboxylic acids of from about 4:1 to 1:2. Further it is also clear that dodecylbenzene sulfonic acid is alone quite effective (Example 5) in our process.

EXAMPLE 12

Use of a High Melting Carboxylic Acid

To a solution of dodecylbenzene sulfonic acid (14.7g) and stearic acid (mp 69° C) (3.3g) in xylene (140 ml) was added Dispal alumina (56.7g). The mixture was heated at reflux for 1 hr., cooled, centrifuged, to remove 1.8g insolubles and concentrated by evaporation of solvent. Yield 99.3g of a product containing 22% aluminum as a moderate viscosity liquid.

We have discovered that the viscosity of the composition of this invention can be reduced by the use of additional lower carboxylic acids, for example acetic, propionic, etc., acids in amounts of about 0.1 to about 50% or more by wgt. of carboxylic acids based on weight of the composition of this invention such as from about 0.5% to 25%, for example by about 0.7 to 15%, but preferably from about 1–10%, with an optimum of about 1–5%.

The following example illustrates viscosity reduction by the use of acetic acid.

EXAMPLE 13

To a solution of stearic acid (6.6g) and dodecylbenzenesulfonic acid (29.4g) in xylene (280 ml) was added Dispal alumina (113.4g) while stirring. After heating at reflux for 1 hour the mixture was cooled and undispersed alumina (3g) was removed by centrifugation. Excess solvent was then removed by distillation to yield a homogenous product 189.3g containing 21.6% aluminum. Viscosity of this product was 4840 centipoise.

To this produce was added acetic acid with the following results:

| Acetic acid (% by wgt.) | Viscosity (centipoise) |
|---|---|
| 0% | 4840 |
| 1.2% | 3800 |
| 1.8% | 2480 |
| 3.1% | 1600 |
| 4.6% | 1280 |
| 6.2% | 1080 |
| 7.0% | 1000 |

Aluminum dispersions produced by the process of the present invention are useful as fuel oil additives, jet fuel additives, motor fuel additives, lubricant additives and the like. The dispersions of the present invention are particularly useful since such dispersions contain substantial amounts of aluminum in a clear bright dispersion suitable for use in high quality motor oils and the like.

The compositions of this invention are particularly effective in the inhibition of vanadium corrosion in gas turbines.

We claim:

1. The process of preparing an oil-soluble aluminum dispersion which comprises reacting alumina with a mixture of oil-soluble sulfonic and carboxylic acids, the mole ratio of sulfonic to carboxylic acids being from about 4:1 to 1:2.

2. The product of the process of claim 1 having an aluminum content of from about 15% to 25%.

3. The process of preparing an oil-soluble aluminum dispersion which comprises reacting alumina with a mixture of oil-soluble sulfonic and carboxylic acids, substantially no water or oleaginous carrier being employed in the reaction.

4. The process of claim 3 where the alumina reacted is prepared by the water hydrolysis of aluminum alkoxides.

5. The process of claim 3 where the carboxylic acids are hydrocarbyl carboxylic acids containing at least 8 carbon atoms.

6. The product of the process of claim 4 having an aluminum content of from about 15% to 25%.

7. The product of the process of claim 5 having an aluminum content of from about 15% to 25%.

8. The product of the process of claim 3 containing additionally a viscosity lowering amount of a lower carboxylic acid.

9. The product of claim 8 where the lower carboxylic acid is acetic acid.

10. The process of claim 3 wherein the reaction is carried out by heating a mixture consisting essentially of oil soluble hydrocarbyl sulfonic acids, oil soluble hydrocarbyl carboxylic acids containing at least 8 carbon atoms, alumina prepared by the water hydrolysis of aluminum alkoxides and a volatile solvent, removing said solvent by distillation, and removing undispersed solids, the mole ratio of sulfonic to carboxylic acids being from about 10:1 to 1:10.

11. The process of claim 10 wherein the molecular weight of the hydrocarbon portion of said sulfonic acid is below 300 and the carboxylic acid is selected from the group consisting of substituted cyclopentane, substituted cyclohexane and substituted polycyclic monocarboxylic acids containing at least 15 carbon atoms and fatty acids containing at least about 8 carbon atoms, and the mole ratio of sulfonic to carboxylic acids is from about 4:1 to 1:4.

12. The product of the process of claim 10.

13. The product of the process of claim 11.

14. The product of the process of claim 10 containing additionally a viscosity lowering amount of a lower carboxylic acid.

15. The product of claim 14 where the lower carboxylic acid is acetic acid.

16. The product of the process of claim 11 containing additionally a viscosity lowering amount of a lower carboxylic acid.

17. The product of claim 16 where the lower carboxylic acid is acetic acid.

* * * * *